US00PP24530P3

(12) United States Plant Patent
Kordes

(10) Patent No.: US PP24,530 P3
(45) Date of Patent: Jun. 10, 2014

(54) SHRUB ROSE PLANT NAMED 'KORPIFLEU'

(50) Latin Name: *Rosa hybrida*
Varietal Denomination: KORpifleu

(75) Inventor: Tim-Hermann Kordes, Klein Offenseth-Sparrieshoop (DE)

(73) Assignee: W. Kordes' Söhne Rosenschuken GmbH & Co KG, Offenseth-Sparrieshoop (DE)

( * ) Notice: Subject to any disclaimer, the term of this patent is extended or adjusted under 35 U.S.C. 154(b) by 78 days.

(21) Appl. No.: 13/507,405

(22) Filed: Jun. 26, 2012

(65) Prior Publication Data

US 2013/0347148 P1 Dec. 26, 2013

(51) Int. Cl.
*A01H 5/00* (2006.01)

(52) U.S. Cl.
USPC ..... Plt./207; Plt./101; Plt./102

(58) Field of Classification Search
USPC ..... Plt./101, 102, 107
See application file for complete search history.

*Primary Examiner* — Susan McCormick Ewoldt

(57) ABSTRACT

A new and distinct variety of rose with novel pink, yellow-centered flowers, and attractive foliage with very good disease resistance. It exhibits moderately vigorous growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpifleu'. The new variety of rose plant of the present invention originated from a controlled crossing in a breeding program of two distinct parents during the summer of 1998. The crossing was between an 'un-named seedling', the seed parent, and another 'un-named seedling', the pollen parent, from the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpifleu'.

CROSS REFERENCES AND FEDERAL R&D STATEMENT

There are no cross referenced or related applications. This variety was developed without the aid of any research grant.

SUMMARY OF THE INVENTION

The new rose plant may be distinguished from its seed parent, an 'un-named seedling', by the following combination of characteristics:

1. The 'un-named seedling' has small pink flowers, whereas 'KORpifleu' has very small pink flowers with yellow centers.
2. The 'un-named seedling' has a semi-double petal count, whereas 'KORpifleu' has a single petal count.

The new rose plant may be distinguished from its pollen parent, an 'un-named seedling', by the following combination of characteristics:

1. 'KORpifleu' has pink flowers with yellow centers, whereas the 'un-named seedling' has orange flowers with yellow centers.
2. 'KORpifleu' has much better disease resistance than the 'un-named seedling'.

The objective of the hybridization was to create a new and distinct rose plant with unique qualities, such as:

1. Uniform growth and flowering;
2. Abundant attractive, recurrent pink flowers with yellow centers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpifleu' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpifleu' was selected in May, 1999 from the seedling beds to be asexually propagated for further evaluation. The first asexual propagation of 'KORpifleu' was done by budding to seedling understocks in July, 1999 at the inventor's nursery in Offenseth-Sparrieshoop, Germany.

This initial and other subsequent propagations conducted in controlled environments demonstrate that 'KORpifleu' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, petals, leaves, prickles, and stems of 'KORpifleu'.

DETAILED BOTANICAL DESCRIPTION

The following is a description of 'KORpifleu', as observed growing in October, 2011 in a nursery in Jackson County, Oreg. on plants 1 year of age. Color references are made using The Royal Horticultural Society (London, England) Colour Chart, 2001 except where common terms of color are used.

For a comparison, several physical characteristics of the rose variety 'KORfullwind', a rose variety from the same inventor described and illustrated in U.S. Plant Pat. No. 8,872 and issued on Aug. 30, 1994 are compared to 'KORpifleu' in Chart 1.

CHART 1

| Characteristic | 'KORpifleu' | 'KORfullwind' |
|---|---|---|
| Petal count | 5 | 15-20 |
| Petal color after opening, inner side | Red-Purple Group 58C | Red Group 49B |
| Petal color after opening, outer side | Red Group 56D with intonations of Red Group 54A on petal margin | Red Group 49B |

Parents:

*Seed parent.*—An 'un-named seedling'.

*Pollen parent.*—An 'un-named seedling'.

Classification:

*Botanical classification.*—*Rosa hybrida* 'KORpifleu'.

*Commercial classification.*—Landscape shrub rose.

FLOWER AND FLOWER BUD

Blooming habit: Recurrent.

Flower bud:

*Size.*—Upon opening, 12 mm in length from base of receptacle to distal end of bud and 11 mm diameter at its widest point.

*Bud form.*—Short. Pointed ovoid.

*Bud color.*—As sepals first unfold, bud color is Red Group 37B with intonations of Red Group 46D. When ¼ open, the upper surface of petals is Red Group 47B, and the lower surface is Red Group 36B with intonations of Red Group 47C and Yellow Group 3B.

*Sepals.*—Color: Upper surface Yellow-Green Group 147D. Lower surface Yellow-Green Group 146B. Size: Average 12-14 mm (l)×4-5 mm (w). Shape: Weak foliaceous appendages on two of the five sepals. Apex: Apiculate. Base: Flat at union with receptacle. Quantity: Five. Surface texture: Upper side: Heavily pubescent. Lower surface: Glabrous with stipitate glands. Margins: With stipitate glands.

Receptacle:

*Surface.*—With fine hairs.

*Color.*—Yellow-Green Group 144 A.

*Shape.*—Urn-shaped.

*Size.*—4 mm (h)×5 mm (w).

Peduncle:

*Surface.*—With stipitate glands.

*Length.*—25 to 35 mm average length.

*Diameter.*—1 to 1.5 mm average diameter.

*Color.*—Yellow-Green Group 144A.

*Strength.*—Strong.

*Borne.*—Multiple flower buds per stem, generally 3 to 6.

Flower bloom:

*Fragrance.*—None.

*Duration.*—On the plant 3 to 4 days. As a cut flower, 2 to 3 days. Senesced petals drop away cleanly.

*Size.*—Small for a landscape shrub rose. When open, the average flower diameter is 45 mm and the average flower height is 8 mm.

*Form.*—Shape of flower when viewed from the side: Upon opening, upper part: Flat. Upon opening, lower part: Flat. Open flower, upper part: Flat. Open flower, lower part: Flat.

Color:

*Upon opening, petals.*—Outer Side: Red Group 36B with intonations of Red Group 46D on petal margin. Inner Side: Red Group 43C.

*Upon opening, basal petal spots.*—Outer Side: Yellow Group 7C. Inner Side: Yellow Group 7A.

*After opening, petals.*—Outer Side: Red Group 56D with intonations of Red Group 54A on petal margin. Inner Side: Red-Purple Group 58C.

*After opening, basal petal spots.*—Outer Side: Yellow Group 4B. Inner Side: Yellow Group 7B.

General tonality: On open flower Red Group 45D. No change in the general tonality at the end of the first day. Afterwards, general tonality is Red-Purple Group 58C.

Petals:

*Petal count.*—Single.

*Average range.*—Approximately 5 petals under normal conditions.

*Petal reflex.*—Petals reflex weakly.

*Petal edge.*—Entire.

*Petal shape.*—Deltoid. Apex shape is obtuse. Shape of base is deltoid.

*Petal size.*—22 mm (l) 25 mm (w).

*Thickness.*—Thin.

*Petal arrangement.*—Not formal.

Petaloids:

*Petaloid count.*—Average of 0 per flower.

Reproductive organs:

*Pistils.*—Few. Approximately 3 to 8 present. Stigmas: Location: Slightly inferior in position to anthers. Color: Yellow-Orange Group 16D. Styles: Length: About 3 mm long. Color: Yellow-Green Group 154D with intonations of Red Group 45D.

*Stamens.*—Approximately 80 to 100 on average and regularly arranged. Anthers: Size: Average 2 mm (l). Pollen: Generally present. Color: Greyed-Orange Group 163B. Filaments: Color: Green-Yellow Group 1B. Length: 5-7 mm.

THE PLANT

*Growth.*—Moderate.

*Plant habit.*—Compact ground cover habit. When grown as a budded field plant on *Rosa multiflora* understock, the average plant height is 25 cm and the average plant width is 45 cm.

*Blooming.*—Prolific.

*Stems.*—Stem color: Young wood: Yellow-Green Group 144A. Older wood: Green Group 137B. Stem surface: Young wood: Smooth. Older wood: Smooth.

*Prickles.*—Present. Incidence: Average of 10 to 12 per each 10 cm of stem. Size: Average length: 8 mm. Color: Immature prickles: Yellow-Green Group 146D. Mature prickles: Yellow-Green Group 146D with anthocyanin intonations of Greyed-Red Group 182D at base of prickle. Shape: Deeply concave. Anthocyanin: On young thorns, Greyed-Purple Group 184B.

*Leaves and leaflets.*—Normally 7 leaflets on normal leaves in middle of the stem. Venation pattern: Pyramidal net pattern. Leaf size: 100 mm (l)×55 mm (w). Abundance: Average. Texture: Smooth. Upper side of: leaf: Glossy and smooth. Under side of: leaf: Matte. Color, mature foliage: Upper Leaf Surface: Green Group 137A. Lower Leaf Surface: Green Group 137C. Color, juvenile foliage: Upper Leaf Surface: Green Group 137A. Lower Leaf Surface: Green Group 137A. Anthocyanin intonation: Present. Intonations of Greyed-Purple Group 183B present on upper sides and margins of juvenile leaflets.

*Stipules.*—Size: 12 mm long, 3 mm from distal tip to distal tip. Stipule color: Green Group 137B. Anthocyanin: Greyed-Purple Group 183C on immature foliage. Margins: With stipitate glands. Shape: Apex: Apiculate. Base: Winged.

*Petiole.*—Length: Average 15 mm. Diameter: Average 1 mm. Petiole color: Yellow-Green Group 146A. Underneath: With prickles and limited stipitate glands. Margins: With stipitate glands. Anthocyanin: Greyed-Purple Group 187B on immature foliage.

*Petiole rachis.*—Length: Average 10 mm. Diameter: Average 1 mm. Color: Yellow-Green Group 146B. Anthocyanin present on juvenile tissue: Greyed-Purple Group 187B. Underneath: With prickles and stipitate glands. Upper side: Pubescent. Margins: With stipitate glands.

*Leaflets.*—Size: Average size of the terminal leaflet is 25 mm (l)×15 mm (w). Shape: Ovate. Base: Obtuse. Apex: Cuspidate. Margins: Finely serrated. Surface: Upper: glossy. Lower: matte. Texture: Smooth. Arrangement: Odd pinnate. Venation Reticulate.

Hips/seed formation: Size: 12 mm (l)×10 mm (w). Color: Yellow-Green Group 144A.

Winter hardiness: To date, the variety has been grown successfully in USDA zones 5-8.

Disease resistance: Very good resistance to Powdery mildew (*Sphaerotheca pannosa*), blackspot (*Diplocarpon rosae*), and *Botrytis* (*Botrytis cinerea*) diseases under normal growing conditions.

I claim:

1. A new and distinct variety of rose plant, as described and illustrated herein.

* * * * *

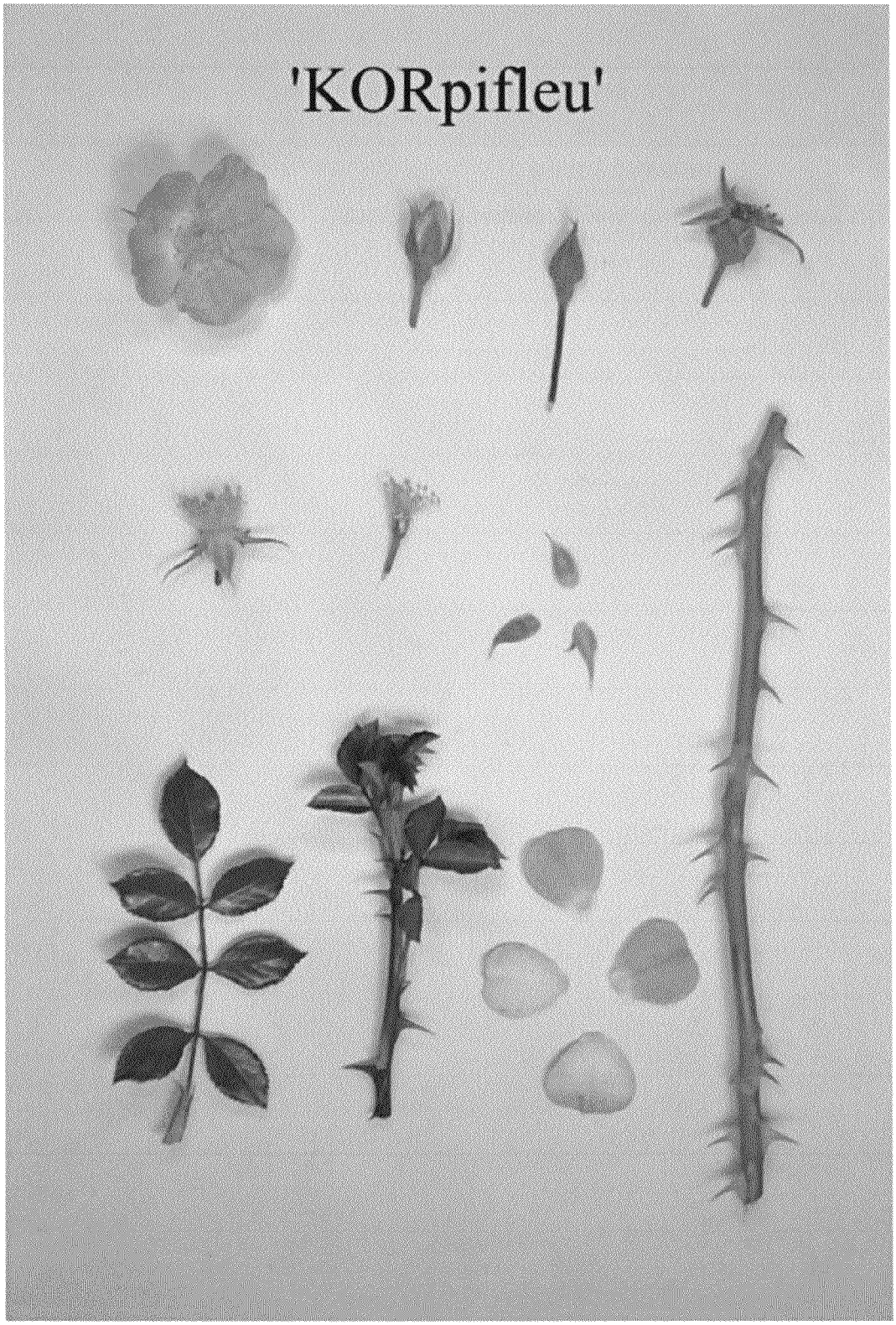
'KORpifleu'